(12) United States Patent
Guo et al.

(10) Patent No.: US 8,680,228 B2
(45) Date of Patent: Mar. 25, 2014

(54) CONTROLLED HYDROLYSIS OF POLY-4-HYDROXYBUTYRATE AND COPOLYMERS

(71) Applicant: Tepha, Inc., Lexington, MA (US)

(72) Inventors: Kai Guo, Brookline, MA (US); David P. Martin, Arlington, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 13/627,545

(22) Filed: Sep. 26, 2012

(65) Prior Publication Data

US 2013/0085185 A1    Apr. 4, 2013

Related U.S. Application Data

(60) Provisional application No. 61/539,695, filed on Sep. 27, 2011.

(51) Int. Cl.
*C08G 63/02* (2006.01)
*C08G 64/00* (2006.01)

(52) U.S. Cl.
USPC ......... 528/271; 264/176.1; 264/179; 528/354

(58) Field of Classification Search
USPC ................ 264/176.1, 179; 528/271, 272, 354
See application file for complete search history.

(56) References Cited

U.S. PATENT DOCUMENTS

| | | | |
|---|---|---|---|
| 5,191,016 A | 3/1993 | Yalpani | |
| 5,811,272 A | 9/1998 | Snell | |
| 6,245,537 B1 | 6/2001 | Williams | |
| 6,316,262 B1 | 11/2001 | Huisman | |
| 6,323,010 B1 | 11/2001 | Skraly | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,730 B1 | 9/2003 | Williams | |
| 6,623,748 B2 | 9/2003 | Clokie | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Martin | |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,553,923 B2 * | 6/2009 | Williams et al. | 528/354 |
| 2002/0141967 A1 | 10/2002 | Williams | |
| 2003/0211131 A1 | 11/2003 | Martin | |
| 2006/0177513 A1 | 8/2006 | Martin | |

FOREIGN PATENT DOCUMENTS

| | | |
|---|---|---|
| WO | 9932536 | 7/1999 |
| WO | 0056376 | 9/2000 |

OTHER PUBLICATIONS

Hori, et al., "Chemical synthesis of high molecular weight poly(3-hydroxybutyrate-co-4-hydroxybutyrate)", Polymer 36:4703-5 (1995).
Houk, et al., "Why delta-valerolactone polymerizes and gamma-butyrolactone does not", J. Org. Chem., 73 (7), 2674-8 (2008).
Martin, et al., "Medical Applications of Poly-4-hydroxybutyrate: A Strong Flexible Absorbable Biomaterial", Biochem. Eng. J. 16:97-105 (2003).
Moore, et al., "Chemosynthesis of bioresorbable poly(gamma-butyrolactone) by ring-opening polymerisation: a review", Biomaterials 26:3771-82 (2005).
Steinbüchel, et al., "Diversity of Bacterial Polyhydroxyalkanoic Acids", FEMS Microbial. Lett. 128:219-28 (1995).
Williams, et al., "Application of PHAs in Medicine and Pharmacy", Polyesters, III, 4:91-127 (2002).
International Search Report and Written Opinion for PCT/US2012/057277 mailed Mar. 11, 2013.

* cited by examiner

*Primary Examiner* — Terressa Boykin
(74) *Attorney, Agent, or Firm* — Pabst Patent Group LLP

(57) ABSTRACT

Methods for making P4HB polymers and copolymers thereof that are useful for preparing controlled release systems, medical devices and as intermediates in chemical synthesis, have been developed. These methods avoid the use of organic solvents, and basic conditions that can cause transesterification reactions with polymer terminal end groups or elimination reactions. A preferred embodiment is a method for producing polymers of P4HB with weight average molecular weight less than 250,000, and more preferably, less than 100,000, and a Pd of less than 3, which are useful in controlled release. A particularly preferred embodiment utilizes aqueous acetic acid to hydrolyze pellets of P4HB polymers and copolymers while in suspension.

17 Claims, 3 Drawing Sheets

Pathway enzymes are:
1. Succinic semialdehyde dehydrogenase,
2. 4-hydroxybutyrate dehydrogenase,
3. Diol oxidoreductase,
4. aldehyde dehydrogenase,
5. Coenzyme A transferase and
6. PHA synthetase.

CONTROLLED HYDROLYSIS OF POLY-4-HYDROXYBUTYRATE AND COPOLYMERS

CROSS REFERENCE TO RELATED APPLICATIONS

This application claims benefit of U.S. Provisional Application No. 61/539,695, filed Sep. 27, 2011, which is hereby incorporated herein by reference in its entirety.

FIELD OF THE INVENTION

The present invention generally relates to methods for controlling the hydrolysis of poly-4-hydroxybutyrate and copolymers thereof, and to compositions of poly-4-hydroxybutyrate and copolymers thereof with specific weight average molecular weights. The compositions can be used in implantable medical devices, controlled release applications, such as drug delivery, and certain compositions may be used for therapeutic delivery of 4-hydroxybutyrate. The compositions may also be used in blends, and as intermediates in synthesis.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure.

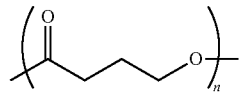

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production. Several biosynthetic routes are currently known to produce P4HB as shown in FIG. 1.

Chemical synthesis of P4HB has been attempted, but it has been impossible to produce the polymer with a sufficiently high molecular weight that is necessary for most applications (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)).

U.S. Pat. Nos. 6,245,537, 6,623,748 and 7,244,442 describe methods of making PHAs with little to no endotoxin, which is suitable for medical applications. U.S. Pat. Nos. 6,548,569, 6,838,493, 6,867,247, 7,268,205, and 7,179,883 describe use of PHAs to make medical devices. Copolymers of P4HB include 4-hydroxybutyrate copolymerized with 3-hydroxybutyrate or glycolic acid (U.S. patent application No. 20030211131 by Martin and Skraly, U.S. Pat. No. 6,316,262 to Huisman et al., and U.S. Pat. No. 6,323,010 to Skraly et al.). Methods to control molecular weight of PHA polymers by biosynthetic methods have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering.

In controlled release there currently exists a need for P4HB and copolymers thereof with narrowly defined weight average molecular weight ranges. By controlling these ranges, compositions can be developed that allow the controlled release of a wide range of bioactive agents. Particularly desired compositions include polymers with weight average molecular weights less than 250,000, and more preferably less than 100,000. Preferably, the compositions should have a polydispersity of less than 3, and more preferably less than 2.5.

In addition to being useful in controlled release, lower molecular weight compositions of P4HB and copolymers thereof can be useful in the preparation of other chemicals, polymers, copolymers, and for blending with other materials. For example, low molecular weight P4HB and copolymers thereof can be used in the preparation of polyurethanes or as nucleants or fillers in blends.

U.S. Pat. No. 6,623,730 to Williams and Martin discloses the use of oligomers of P4HB as prodrugs to modulate endogenous levels of 4-hydroxybutyrate, and methods to prepare these oligomers by hydrolysis of P4HB. The method disclosed uses aliquots of sodium methoxide to hydrolyze P4HB dissolved in a solvent (anhydrous THF) to provide the oligomers of P4HB of the desired molecular weight. Starting with a polymer of molecular weight 430,000 g/mol, sodium methoxide is used to produce P4HB molecular weights of 320,000, 82,000 and 25,000. The disadvantages of this procedure are as follows: (i) the use of methoxide can result in terminal esterification of the polyester chains (producing methyl esters); (ii) the relatively low solubility of P4HB in THF (and other solvents) requires large volumes of solvent to dissolve the polymer which is difficult to handle, expensive, and costly to remove; and (iii) basic conditions could potentially lead to elimination reactions in the polymer causing unwanted side reactions.

It is an object of the present invention to provide methods to produce P4HB and copolymers thereof by hydrolysis of high molecular weight P4HB and copolymers without the use of solvents.

It is a further object of the present invention to provide methods to produce P4HB and copolymers thereof by hydrolysis of high molecular weight P4HB and copolymers without the use of basic conditions that can esterify polymer terminal end groups or cause basic elimination in the polymer chains.

It is another object of the present invention to provide methods for hydrolysis of P4HB and copolymers thereof that maintain the polymers in solid state during hydrolysis resulting in easy isolation of the hydrolyzed products.

It is still another object of the present invention to provide compositions of P4HB and copolymers thereof that can be used in medical applications, for example, in implantable medical devices and or for the controlled release of bioactive substances, including the controlled release of 4-hydroxybutyrate.

SUMMARY OF THE INVENTION

Methods for making P4HB polymers and copolymers thereof that are useful for preparing controlled release systems, and as intermediates in chemical synthesis, have been developed. These methods avoid the use of organic solvents, and basic conditions that can cause transesterification reactions with polymer terminal end groups or elimination reactions. A preferred embodiment is a method for producing polymers of P4HB with weight average molecular weight less than 250,000, and more preferably, less than 100,000, which are useful in controlled release. A particularly preferred embodiment utilizes aqueous acetic acid to hydrolyze pellets of P4HB polymers and copolymers while in suspension.

DETAILED DESCRIPTION OF THE INVENTION

Definitions

Figure 1:
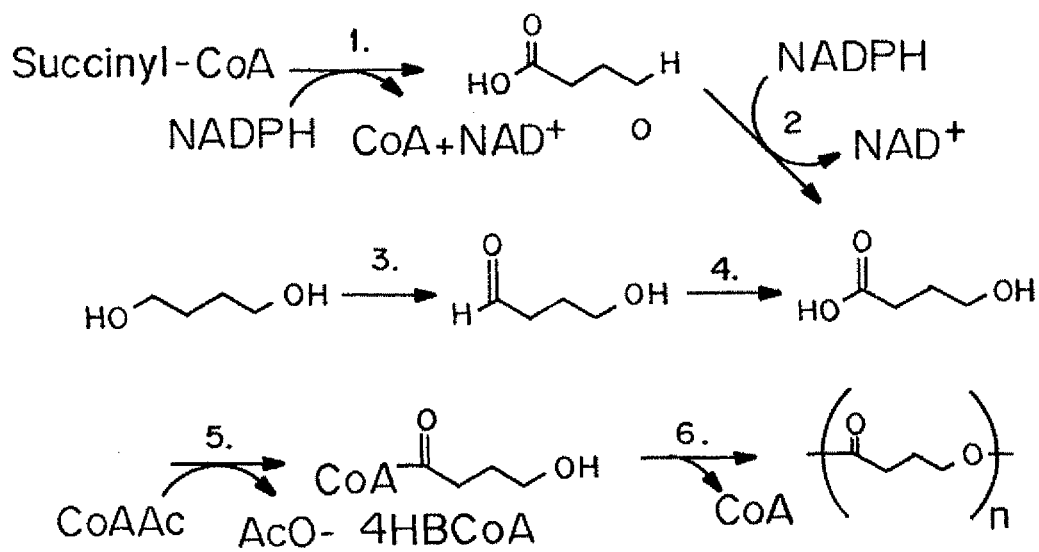
FIG. 1 is a diagram of pathways leading to the biosynthesis of poly-4-hydroxybutyrate.

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Lexington, Mass.).

"Copolymers of poly-4-hydroxybutyrate" as generally used herein means any polymer comprising 4-hydroxybutyrate with one or more different hydroxy acid units.

"Controlled release" or "modified release, as used herein, refers to a release profile in which the drug release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, aptamers, siRNA, nucleic acids, and combinations thereof. "Bioactive agent" includes a single such agent and is also intended to include a plurality "Blend" as generally used herein means a physical combination of different polymers, as opposed to a copolymer comprised of two or more different monomers.

"Molecular weight" as used herein, unless otherwise specified, refers to the weight average molecular weight (Mw), not the number average molecular weight (Mn), and is measured by gel permeation chromatography (GPC) relative to polystyrene.

"Absorbable" as generally used herein means the material is broken down in the body and eventually eliminated from the body within 5 years.

"Biocompatible" as generally used herein means the biological response to the material or device being appropriate for the device's intended application in vivo. Any metabolites of these materials should also be biocompatible.

I. Composition

Methods have been developed to produce low molecular weight (Mw) compositions of P4HB and copolymers thereof in high yield. These methods may be used to prepare P4HB and copolymers thereof with weight average molecular weights (Mw) ranging from 1 to 250 kDa, and more preferably with Mw ranging from 5 to 100 kDa. The methods also yield P4HB and copolymers with narrow polydispersity (PDI), less than 3.0 and preferably a PDI of less than 2.5. The P4HB and copolymers thereof are prepared by hydrolysis with aqueous acids, and preferably with acetic acid. A major advantage of the method is that pellets of the polymers may be suspended in acid, and hydrolyzed while in suspension to yield polymers of predictable weight average molecular weight and narrow polydispersity. In addition, purification is straightforward, side reactions are essentially absent, and yields are very high.

A. Polymers

The processes described herein can typically be used with poly-4-hydroxybutyrate (P4HB) or a copolymer thereof. Copolymers include P4HB with another hydroxyacid, such as 3-hydroxybutyrate, and P4HB with glycolic acid or lactic acid monomer. P4HB and copolymers thereof can be obtained from Tepha, Inc. of Lexington, Mass.

In a preferred embodiment, the starting P4HB homopolymer and copolymers thereof are extruded into pellets. An extruder can be used for this purpose. The pellets are then suspended in acid for hydrolysis. This facilitates isolation of the product, and provides a high yield of lower molecular weight product.

B. Hydrolysis

In a preferred embodiment, P4HB and copolymers thereof can be prepared with a weight average molecular weight less than 250,000, and more preferably, less than 100,000. It has been discovered that low molecular weight ($M_w$) polymers and copolymers of P4HB can be produced with unexpectedly high yields, without solvent, and in high purity with side reactions essentially absent. Notably, the hydrolysis can be controlled so that lower molecular weight ($M_w$) polymers and copolymers can be predictably produced with high purity, high yield, and with narrow polydispersity.

The polymers can be hydrolyzed by suspending the polymer in an acid or an acid solution. Therefore, in one embodiment, the acid or acid solution is one in which the polymer pellet is insoluble or partially insoluble. The acid can be an organic acid or an inorganic acid. For those embodiments where the acid is an organic acid, the acid can be a monocarboxylic acid or a polycarboxylic acid, such as a di- or tricarboxylic acid. Suitable organic acids include, but are not limited to, acetic acid, halogenated acetic acid, such as mono-, di-, trihalogenated acetic acid, lactic acid, glycolic acid, propanoic acid, butanoic acid, pentanoic acid, hexanoic acid, benzoic acid, fumaric acid, maleic acid, tartaric acid, citric acid, malic acid, and pyruvic acid. Suitable inorganic acids include, but are not limited to, hydrochloric acid, sulfuric acid, hydrobromic acid, and hydroiodic acid.

A particularly preferred embodiment utilizes aqueous acetic acid to hydrolyze P4HB polymers and copolymers. More preferably, the polymers and copolymers are first extruded into pellets, and then suspended in aqueous acid. It has been discovered that the pellets will remain suspended in the acid (with shaking or stirring) during hydrolysis as the molecular weights of the polymers decrease in a predictable manner. Even though the polymers and copolymers remain suspended, and the polymer does not dissolve, the polydispersity of the lower molecular weight ($M_w$) product remains narrow. Because the pellets do not dissolve in the acid, the product may be easily isolated at the end of the hydrolysis, for example, by decanting, washing with water, and drying. There is no need to evaporate acid or solvent, or use a solvent extraction process to recover the low molecular weight polymers.

Granules or other non-pelletized forms of the polymer or copolymers can be hydrolyzed with the method, however, these forms are more likely to become sticky during hydrolysis, making isolation of the product more difficult.

In a preferred method, the polymer or copolymer pellets are suspended in aqueous acetic acid, and either stirred or shaken. The hydrolysis may be performed at ambient or elevated temperature. Preferably the hydrolysis is undertaken at constant temperature in the range of 37 to 50° C.

The strength of the acid may be adjusted to speed up or slow down the rate of hydrolysis of the polymers and copolymers. In a preferred method, acetic acid is used with a concentration in the range of 5M to 12M. However, lower concentrations may be used to slow down the rate of hydrolysis, and higher concentrations may be used to speed up the rate of hydrolysis.

The length of the hydrolysis reaction will be determined by the molecular weight ($M_w$) desired, form of the polymer or copolymer, temperature of the reaction, type of acid, and concentration of the acid. For example, pellets of P4HB ($M_w$=346 kDa) suspended in aqueous acetic acid at 37° C. for 4 hours will have a $M_w$=224 kDa if the concentration of the acid is 10M, and $M_w$=115 kDA if the concentration of the acid is 12M. Under the same conditions, at 27.5 hours, the molecular weights (Mw) of the polymer with 10M and 12M acetic acid are 85 kDa and 40 kDa, respectively.

C. Uses of Low Molecular Weight P4HB and P4HB Copolymers

Low molecular weight polymers and copolymers of P4HB have properties that are substantially improved for many medical applications relative to higher molecular weight versions. These materials have lower melt viscosities, and higher solubilities in solvents that can make them easier to process. The lower molecular weight P4HB polymer and copolymers thereof can also provide more desirable controlled release profiles for delivery of therapeutic, prophylactic or diagnostic agents or other bioactive agent, such as a small-molecule drug, peptide, protein, antibody, sugar, polysaccharide, nucleotide, oligonucleotide, aptamer, siRNA, nucleic acid, and combinations thereof. The lower molecular weight P4HB may also be used to make medical devices, such as, but not limited to, sutures, stents, stent grafts, stent coatings, devices for temporary wound or tissue support, devices for soft or hard tissue repair, repair patches, tissue engineering scaffolds, retention membranes, anti-adhesion membranes tissue separation membranes, hernia repair devices, device coatings, cardiovascular patches, catheter balloons, vascular closure devices, slings, biocompatible coatings, rotator cuff repair devices, meniscus repair devices, adhesion barriers, guided tissue repair/regeneration devices, articular cartilage repair devices, nerve guides, tendon repair devices, intracardiac septal defect repair devices, including, but not limited to, atrial septal defect repair devices and PFO (patent foramen ovale) closure devices, left atrial appendage (LAA) closure devices, pericardial patches, bulking and filling agents, plastic surgery devices (including facial and breast cosmetic and reconstructive devices), vein valves, heart valves, bone marrow scaffolds, meniscus regeneration devices, ligament and tendon grafts, ocular cell implants, spinal fusion devices, imaging devices, skin substitutes, dural substitutes, bone graft substitutes, wound dressings, and hemostats.

Lower molecular weight polymers and copolymers of P4HB and copolymers thereof can also be used to modulate endogenous levels of 4-hydroxybutyrate as disclosed by U.S. Pat. No. 6,623,730 to Williams and Martin.

Lower molecular weight polymers and copolymers of P4HB and copolymers thereof can also be used in implantable applications that require a more rapid rate of degradation or absorption than the higher Mw polymers. Preferrably, the implanted device will degrade and the low Mw polymer will be absorbed within six months P4HB polymers and copolymers with low molecular weights may also be used in blends with other materials to improve polymer properties. The low molecular polymers may also be used in the synthesis of other materials, for example, in reactive polymerization.

II. Methods of Manufacturing Low Molecular Weight P4HB and Copolymers.

A. Method of Making Low Molecular Weight P4HB Polymer

In a preferred method, a low molecular weight ($M_w$) P4HB polymer or copolymer may be prepared as follows. Pellets of a P4HB polymer are suspended in aqueous acetic acid, and placed in a shaker incubator. A number of parameters can be varied to control the hydrolysis of the polymer or copolymer including, but not limited to, the concentration of the acid, the type of acid, the temperature of the reaction, the speed (rpm) of the shaker (or stirrer speed), and the reaction time.

When the desired molecular weight ($M_w$) is achieved, the reaction is quenched by decanting the acid, and rinsing the polymer or copolymer with water. Residual acid and water may be removed by drying in vacuo.

The present invention will be further understood by reference to the following non-limiting examples.

Example 1

Hydrolysis of P4HB with 12M Aqueous Acetic Acid

Materials and Methods 30 grams of P4HB pellets (Tepha, Inc., Lexington, Mass.) ($M_w$ 367 kDa) were suspended in 100 mL of 12 M aqueous acetic acid (AcOH), and incubated at 37° C. at 50 rpm in a shaker incubator. After 4 and 27.5 hours, the Mw of polymer samples taken from the reaction were 115 and 40 kDa, respectively.

Results

After 4 hours the P4HB pellets became sticky and the AcOH solution turned cloudy. After 30 hours, the whole reaction mixture appeared milky, and when cooled down, it gelled into a semi-solid. It was therefore determined that 12

M AcOH is too strong to be used as the hydrolysis medium for P4HB pellets since this concentration may partially dissolve the polymer. As a result, the collection of the hydrolysis products would less practical and the reaction conditions would be less homogeneous with some hydrolysis occurring in solution and some in the solid phase (i.e. within the pellets).

Example 2

Hydrolysis of P4HB with 10 M Aqueous Acetic Acid

Materials and Methods 30 grams of P4HB pellets (Tepha, Inc., Lexington, Mass.) ($M_w$ 367 kDa) were suspended in 100 mL of 10 M aqueous acetic acid, and incubated at 37° C. at 50 rpm in a shaker incubator. A sample was removed after 4 hours, and the weight average molecular weight of the polymer was determined by GPC (relative to polystyrene) to be 224 kDa. After 27.5 hours, the reaction was quenched by decanting the acetic acid, and rinsing the polymer with distilled water.

Results

The pellets did not clump or aggregate during the reaction time, as was seen for the similar reaction performed in 12 M acetic acid. The polymer pellets were then dried in vacuo to remove residual acetic acid and water.

The weight average molecular weight of the polymer was determined to be 85 kDa after 27.5 hours, and the polymer was recovered in high yield and without loss of material.

Example 3

Hydrolysis of P4HB with 8M Aqueous Acetic Acid

Materials and Methods

A 20 gram sample of P4HB pellets (Tepha, Inc., Lexington, Mass.) ($M_w$ 347 kDa) was suspended in 200 mL of 8 M aqueous acetic acid, and shaken at 50 rpm at 37° C. in a shaker incubator. Samples were removed periodically, and the weight average molecular weight of the polymer and polydispersity were determined by GPC (relative to polystyrene).

Results

The results are tabulated below (time in hours).

TABLE 1

Molecular Weight and PDI of P4HB over Time

| | 8M, 40° C., oil bath, Pellets | |
|---|---|---|
| | $M_w$ (kDa) | PDI |
| 0 | 347 | 2.13 |
| 1 | 335 | 2.15 |
| 2 | 315 | 2.10 |
| 4 | 284 | 2.17 |
| 6 | 263 | 2.08 |
| 8 | 255 | 2.05 |
| 24 | 161 | 1.97 |
| 96 | 68 | 1.90 |
| 120 | 60 | 1.94 |

Example 4

Hydrolysis of P4HB With SM Aqueous Acetic Acid

Materials and Methods

A 20 gram sample of P4HB granules (Tepha, Inc., Lexington, Mass.) ($M_w$ 347 kDa) was suspended in 200 mL of 5M aqueous acetic acid, and stirred at 45° C. Samples were removed periodically, and the weight average molecular weight of the polymer was determined by GPC (relative to polystyrene).

Results

The results (average of three runs) are tabulated in Table 2.

TABLE 2

Molecular Weight and PDI of P4HB over Time

| | 5M, 45° C., Granules | |
|---|---|---|
| Time (hours) | Mw (kDa) | PD |
| 0 | 347 | 2.13 |
| 4 | 280 | 2.12 |
| 22 | 168 | 2.03 |
| 29 | 137 | 1.98 |
| 96 | 60 | 2.01 |

Example 5

H-NMR Analysis of P4HB Acetic Acid Hydrolysis Product

Figure 2A:
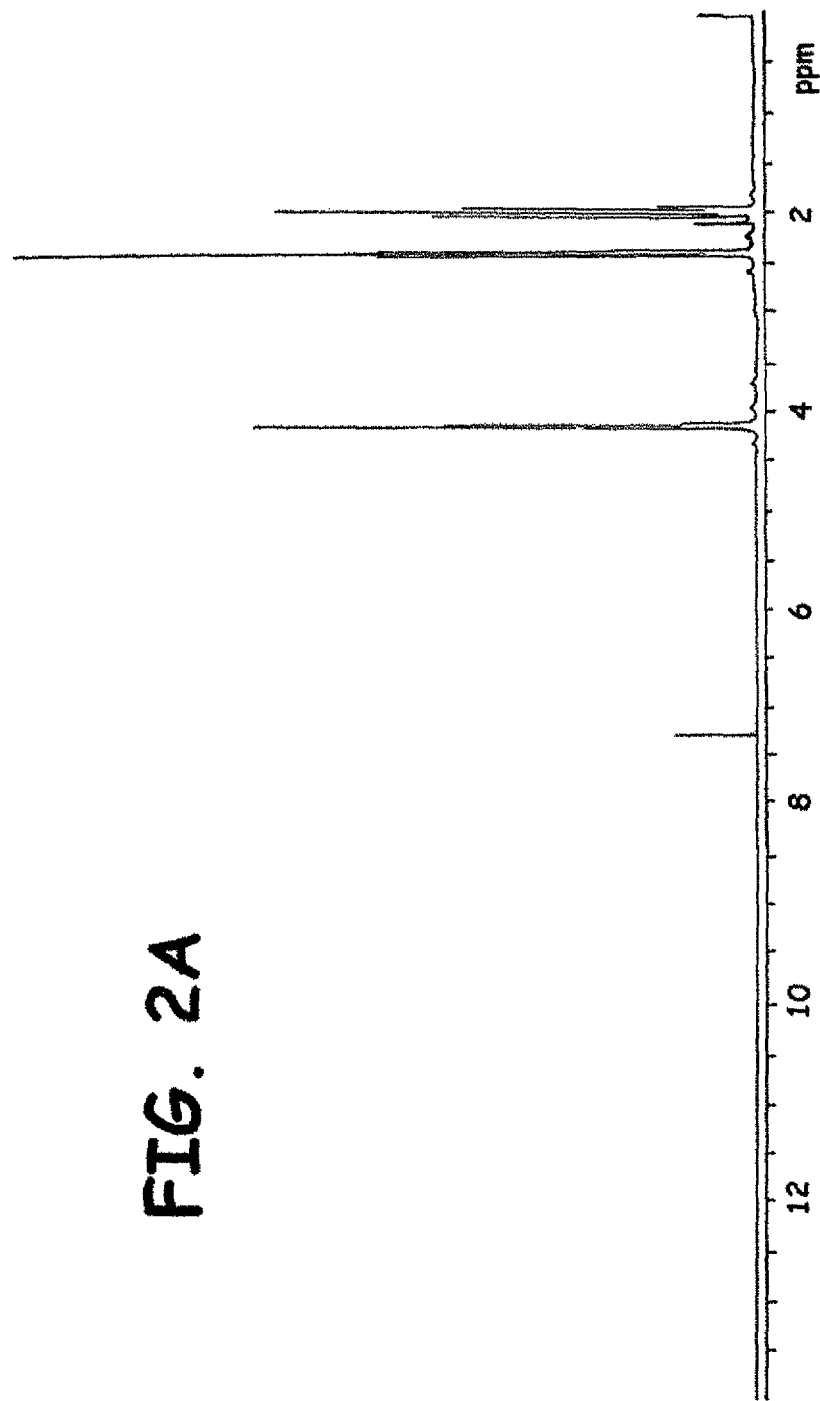
FIG. 2A is a 1H NMR spectrum of the hydrolysis product of P4HB in acetic acid for 27.5 hours from Example 2.
Figure 2B:
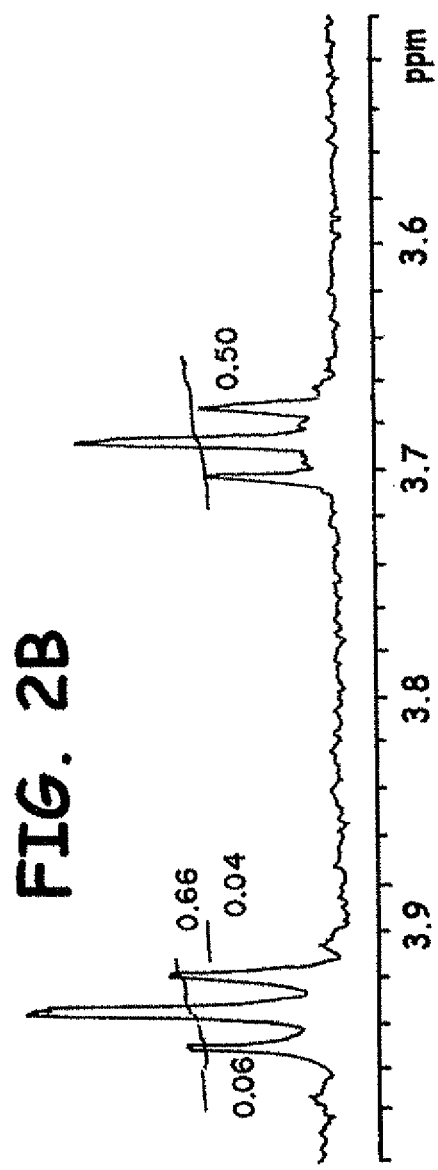
FIG. 2B is an expanded view of the spectrum of FIG. 2A showing the small peaks in the region between approximately 3.5-4.0 ppm.

The $^1$H NMR spectrum of the hydrolysis product from Example 2 after 27.5 hours is shown in FIG. 2. As expected, this low Mw hydrolysis product shows a small $^1$H peak of the polymer end group —$CH_2OH$ at a chemical shift of about 3.69 ppm. The integration area of this peak is 0.50 compared to an integration area of about 100 for the polymer methylene group at chemical shift of about 4.12 ppm. As such, the end group ratio of this sample is 0.5/100, or 0.005, which would suggest the product is a 200 mer (i.e. approx. Mn 17 kDa). This value of Mn from end group analysis is reasonable considering the polymer's GPC $M_w$ of 85 kDa $M_n$ and of 44 kDa. (Note: The GPC values relative to PS are about double the absolute values for the polymer from LLS).

The hydrolysis of P4HB pellets or granules suspended in aqueous solution of acetic acid has been performed successfully under mild conditions with reasonable reaction times. The hydrolysis product, low Mw P4HB, was prepared in a high yield, close to 100%, and its Mw could also be predicted based on the Mw versus reaction time curve under fixed reaction conditions, i.e., temperature and concentration of AcOH. Surprisingly for a biphasic reaction, the polydispersity of the hydrolysis products are low and similar to that of the starting polymer, about 2, showing that the hydrolysis reaction occurs uniformly throughout the bulk of the material, rather than being localized to the surface, even though the pellets/granules remain un-dissolved and suspended in the acetic acid solution.

From the NMR analysis, it appears that the end groups are hydroxyl groups just like the starting polymer. This shows that no new functional groups (i.e. acetate groups) have been added to the polymer and confirms the reaction as a true hydrolysis with no derivatization of the terminal end groups.

The kinetics of the hydrolysis reaction could be affected by a couple of factors such as the reaction temperature (room temperature to 50° C.) and the concentration of AcOH solution (5~10 M). Because the P4HB pellets/granules were simply suspended in the AcOH solution at relative low temperatures instead of forming a homogeneous solution and the ratio of P4HB/AcOH could be 3 g/10 mL, the hydrolysis reaction described herein should be scalable for production of P4HB oligomer with controlled molecular weight.

Modifications and variations of the methods and materials described herein will be obvious to those skilled in the art and are intended to come within the scope of the appended claims. All references cited herein are specifically incorporated by reference.

We claim:

1. A poly-4-hydroxybutyrate polymer or copolymer thereof, wherein the polymer or copolymer is obtained by acidic hydrolysis of a higher molecular weight poly-4-hydroxybutyrate polymer or copolymer suspension in an aqueous solution of the acid and isolating the polymer or copolymer, and wherein the polymer or copolymer has a weight average molecular weight between 1,000 and 250,000 Da and a polydispersity of between 3 and 1.

2. A medical device comprising the polymer or copolymer of claim 1.

3. The device of claim 2 selected from the group consisting of a suture, stent, stent graft, stent coating, drug delivery device, device for temporary wound or tissue support, device for soft or hard tissue repair, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, including but not limited to atrial septal defect repair devices and PFO (patent foramen ovale) closure devices, left atrial appendage (LAA) closure device, pericardial patch, bulking and filling agent, plastic surgery devices (including facial and breast cosmetic and reconstructive devices), vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

4. The device of claim 2 wherein the device is used for controlled release of a bioactive agent.

5. The device of claim 4 wherein the bioactive agent is a therapeutic, prophylactic, and/or diagnostic agent.

6. The device of claim 5 wherein the bioactive agent is a small-molecule drug, peptide, protein, antibody, sugar, polysaccharide, nucleotide, oligonucleotide, aptamer, siRNA, nucleic acid, and combinations thereof.

7. The device of claim 5 wherein the device is used to raise endogenous levels of 4-hydroxybutyrate in a patient.

8. The polymer or copolymer of claim 1 used as an additive or in a polymer blend.

9. A method of using a device, comprising administering to or implanting in an individual in need thereof the device of claim 2.

10. A medical device comprising a poly-4-hydroxybutrate polymer or copolymer, wherein the polymer or copolymer is derived by acidic hydrolysis, and wherein the polymer or copolymer has a weight average molecular weight less than 250,000 Da, and wherein the polymer or copolymer has a polydispersity between 3 and 1.

11. The polymer of claim 1, wherein the copolymer is a copolymer of 4HB and another hydroxy acid.

12. The polymer of claim 11, wherein the hydroxy acid is selected from the group consisting of 3-hydroxybutyrate, glycolic acid, lactic acid, or combinations thereof.

13. A method of making a lower molecular weight poly-4-hydroxybutyrate polymer or copolymer thereof, the method comprising suspending a higher molecular weight polymer or copolymer in an aqueous solution acid to hydrolyze the polymer to form a lower molecular weight polymer or copolymer and isolating the polymer.

14. The method of claim 13, wherein the polymer is hydrolyzed at a temperature from about 37° C. to about 50° C.

15. The method of claim 13 wherein the polymer or copolymer is suspended as pellets or particles for a period of time and at a temperature to hydrolyze the polymer.

16. The method of claim 15, wherein the polymer or copolymer are in pellet form.

17. The method of claim 13 wherein the acid is acetic acid.

* * * * *